United States Patent [19]
Jordan

[11] Patent Number: 6,017,699
[45] Date of Patent: *Jan. 25, 2000

[54] PCR IDENTIFICATION AND QUANTIFICATION OF IMPORTANT CANDIDA SPECIES

[75] Inventor: Jeanne A. Jordan, Pittsburgh, Pa.

[73] Assignee: The University of Pittsburgh, Pittsburgh, Pa.

[*] Notice: This patent is subject to a terminal disclaimer.

[21] Appl. No.: 08/624,290

[22] Filed: Mar. 29, 1996

Related U.S. Application Data

[63] Continuation-in-part of application No. 08/491,641, Jun. 19, 1995, abandoned, which is a continuation of application No. 08/120,780, Sep. 15, 1993, Pat. No. 5,426,026.

[51] Int. Cl.⁷ ...................................................... C12Q 1/68
[52] U.S. Cl. ............................ 435/6; 536/24.31; 435/921
[58] Field of Search ................................ 435/6, 921, 922, 435/923, 924; 536/24.31, 24.33

[56] References Cited

U.S. PATENT DOCUMENTS

| | | | |
|---|---|---|---|
| 5,426,026 | 6/1995 | Jordan | 435/6 |
| 5,426,027 | 6/1995 | Lott et al. | 435/6 |

*Primary Examiner*—Scott W. Houtteman
*Attorney, Agent, or Firm*—Cushman Darby & Cushman IP Group of Pillsbury Madison & Sutro, LLP

[57] ABSTRACT

The subject invention relates to a set of DNA primers which, when utilized in conjunction with the polymerase chain reaction (PCR) assay, can amplify and speciate DNA from five medically important Candida species. Furthermore, the PCR amplified products, generated by the primers, can also be used to create species specific probes which can also detect and confirm the five species of Candida. Thus, the present invention allows for early diagnosis and treatment of an infection. The assay is useful in the context of monitoring antifungal treatment regimens, screening potential antifungal agents, and similar applications requiring quantitative determinations.

38 Claims, 5 Drawing Sheets

L    I    R

PCR IDENTIFICATION AND QUANTIFICATION OF IMPORTANT CANDIDA SPECIES

This is a Continuation-in-Part of National application Ser. No. 08/491,641 filed Jun. 19, 1995 now abandoned, which is a continuation of U.S. application Ser. No. 08/120,780, now U.S. Pat. No. 5,426,026.

BACKGROUND OF THE INVENTION

This application is a continuation-in-part application of Ser. No. 08/491,641, filed Jun. 19, 1995 now abandoned, which is a continuation of Ser. No. 08/120,780, filed Sep. 15, 1993, now U.S. Pat. No. 5,426,026.

FIELD OF THE INVENTION

The subject invention relates to PCR (polymerase chain reaction) based assays and kits which involve a novel set of oligonucleotides which can distinguish and quantitate medically important Candida species.

BACKGROUND INFORMATION

Diagnosing and treating systemic candida infection continues to be a major challenge for the clinician and the microbiologist. It is not only critical to identify the type of candida but also to determine its relative amount. This quantitative data provides insight as to the extent of the infection which in turn provides data as to the degree of fungal load present in a patient which in turn must be eliminated by anti-fungal therapy. The contents of all publications and U.S. patents referred to hereinafter are hereby incorporated by reference.

Classic Methods for the Detection of Candida Sp.

Currently, the gold standard for diagnosing systemic candidiasis is to recover the organism by routine blood culturing (Kiehn et al., *J. Clin. Microbiol.* 14:681–83 (1981); Roberts et al., *J. Clin. Microbiol.* 1:309–10 (1975)). This technique is not always satisfactory in detecting infection early, a critical point for successful outcome in treating systemic candidiasis. In fact, 40–60% of all blood cultures remain negative for Candida despite widespread visceral infection ("Systemic Candidiasis" in *Candidiasis*, eds., Bodey et al., Raven Press, New York (1985)).

Furthermore, in addition to the time required to grow the yeast from blood culture, time is needed to identify and speciate the organism. All of this testing can become a very lengthy process, leaving the infection unchecked in the patient, leading to an increased fungal load. (Fraser, V. J., Jones M., Dunkel J., et al.: "Candidemia in a Tertiary Care Hospital: Epidemiology, Risk Factors, and Predictors of Mortality", *Clin. Inf. Dis.* (1992), vol. 15, p. 414–21).

Unlike the comparative safety of antibiotics, antifungal drugs are quite toxic. Therefore, physicians usually require substantial documentation of fungal infection before they are willing to initiate antifungal therapy. Prompt detection of candidiasis would enable earlier treatment initiation on a smaller fungal load. Thus, timely detection and speciation of Candida infections is crucial for successful treatment using antifungal agents especially in the premature newborn and the immunosuppressed population (i.e., bone marrow transplant patients, AIDS patients, etc.).

PCR-Based Assays Suitable for Detection of Candida Sp.

It is the amplification property of the polymerase chain reaction (PCR) assay together with its short turnaround time that makes it ideal for diagnosing candidemia from minimal sample size volumes. PCR is an efficient, in-vitro method for amplifying DNA from clinical samples that can be tailor-made to suit the needs of any diagnostic laboratory (see U.S. Pat. Nos. 4,683,202 and 4,683,195). Buchman et al. was the first group to describe the use of PCR to identify *Candida albicans* from clinical specimens. These investigators used PCR to amplify a portion of a yeast-specific gene cytochrome lanosterol-14α-demethylase (Buchman et al., *Surgery* 108:338–47 (1990)).

More specifically, Buchman et al. utilized a set of primers that amplified the *Candida albicans* cytochrome $P_{450}$ $L_1A_1$ (lanosterol-14α-demethylase) gene. The predicted product size was estimated to be 240 base pairs. However, aberrant and unexplained amplification patterns were seen in various clinical specimens containing *C. albicans* DNA.

In addition, the primer set utilized by Buchman et al. amplified DNA from other non-albicans species giving rise to some PCR products of the "predicted" 240 bp size and some of alternate sizes. Other non-albican species gave no 240 bp fragment but just a variety of alternate-sized products. There was no consistency in the size of the PCR products generated using this primer set.

Fujita et al., in an article entitled "Microtitration Plate Assay to Detect PCR-Amplified DNA from Candida Species in Blood," appearing in J. Clinical Microbiology, Vol. 33, No. 4, at pages 962–967, report a study where nonisotopic, digoxigenin-labelled oligonucleotide probes were designed on the basis of the sequence of the ITS2 region of *C. ablicans, C. tropicalis, C. parapsilosis, C. krusei,* and *C. glabrata* rDNA. These probes were then used in a microtitration plate assay to rapidly detect and identify amplified genomic DNA from *C. ablicans* blastoconidia introduced into blood.

Other hybridization based assays relevant to Candida are taught in U.S. Pat. Nos. 5,405,745 (Gorman et al.) and 5,403,710 (Weisburg et al). The Weisburg group focuses on development a specific set of probes which selectively hybridize to rDNA (ribosomal DNA) of Candida as compared to other fungi or bacteria present in samples. Certain probes distinguish Candida species types. The Gorman group also developed a set of probes which distinguish Candida species. A quantitative technique is taught which employs an LKB scanning densitometer.

Quantitative PCR-Based Assays

Quantitative methods employing PCR are known. The main constraint in obtaining accurate quantitative data is inherent in the amplification process. Because amplification is (at least initially) an exponential process, small difference in any of the variables that control the reaction rate will dramatically affect the yield of the PCR product. These variables include the concentration of polymerase, dNTPs, $Mg^{+2}$, DNA and primers, annealing, extension and denaturing temperatures; cycle length and cycle number; ramping times; rate of "primer-dimer" formation and the presence of contaminating DNA. Even when all these variables are controlled precisely, there is sometimes tube to tube variations that precludes accurate quantitation.

Co-amplification of a competitive substrate is a technique used to quantitate sample. The competitive substrate functions as an internal standard. The strategy involves co-amplification of a competitive template that uses the same primers as those of the target cDNA but can be distinguished from the target cDNA after amplification. Since a change in any of the variables previously listed will affect the yield of the competitive template equally, relative ratios of the two should be preserved with amplification.

Other quantification PCR techniques are exemplified in Nireleau et al., *Nucleic Acids Research*, 1994, Vol. 22, No. 44, pp. 5508–5509 and Berry et al., "HIV Type 2 Proviral Load Measured and by Quantitative Polymerase Chain Reaction Correlates with CD4 Lymphopenia in HIV Type 2-Invented Individuals", *AIDS Research and Human Retroviruses*, Vol. 10, No. 8 (1994), pp. 1031–1037.

SUMMARY OF THE INVENTION

The present invention relates to a new set of probes and their use in test kits and in sensitive and rapid PCR-based assay to detect and distinguish *C. parapsilosis, C. tropicalis, C. glabrata,* and *C. krusei*. The present invention also relates to an improved universally applicable plate-based assay format which enhances sensitivity and is suitable for use with a variety of probe types. The invention also relates to a means of monitoring the progress of the antifungal treatment regimen using PCR based assays.

The assays of the invention can be employed advantageously to test a variety of sample types including genital swabs, blood, urine, cerebrospinal fluid, skin biopsy, saliva, synovial fluid, sputum, bronchial wash and bronchial lavage. The general procedures for nucleic acid isolation specimen preparation are well known in the art, and are described by F. C. Odds (in *Candida and Candidiasis, A Review and Bibliography*; 2nd edition (1988) Buillieri Tindall).

The work reflected in the parent application Ser. No. 08/120,780 involved a single pair of DNA primers which was designed from the published sequence of the chitin synthase gene CHS1 of *Candida albicans* (Au-Young et al, *Mol. Microbiol.*, vol. 4, p. 197–207 (1990)). This primer set was successfully used to amplify uniquely-sized DNA products from not only *Candida albicans,* but from *Candida glabrata, Candida parapsilosis,* and *Candida tropicalis* as well (see FIG. 1). (These four Candida species are responsible for more than 95% of all neonatal infections caused by Candida (Butler, *Pediatr. Clin. North Am.* vol. 35, p. 543–63 (1988), Faix, *J. Pediatr.* vol. 105, p. 616–22 (1984)).) Subsequent DNA sequencing of these amplified products allowed for the design of three species-specific DNA primers for amplification of DNA isolated from *Candida glabrata, Candida parapsilosis* or *Candida tropicalis*. However, there still existed a need for probes to identify *Candida krusei*. This application reflects this additional work.

The results of the PCR based assay using a single primer pair reported in the parent application correlated well with a retrospective study of 14 children or neonates with culture proven candidemia. The PCR and culture results were identical in 24 of the 25 blood samples tested (see Table 2). This high degree of correlation between PCR and culture substantiated the use of PCR as being as accurate as culture methods in diagnosing systemic Candidiasis with the additional benefits of greater sensitivity and rapidity.

The four species-specific DNA probes reported in the parent application have the following DNA sequences (see SEQ ID NOS:3, 4, 5, and 6, respectively)

CA 5'-CGT TCG TAC TAG AGT TGT GTT GTT TTG GAT-3',

CG 5'-CGA CTG GTT GAC GAT AAT CAG AGG AGA TGG G-3',

CP 5'-GAG GCT GTG ATG TGT GCT GTT GAC CAG-3', and

CT 5'-AGG CTT GCT CTT TGT CGG GCG AGC GAA CG-3'.

Each sequence hybridizes to an internal portion of the amplified chitin synthase 1 gene of *Candida albicans, Candida glabrata, Candida parapsilosis,* and *Candida tropicalis,* respectively.

New Probe Construction
Generation of Five Species-Specific Primers and Probes A previously described primer pair was used to generate amplified products of the following sizes from the chitin synthase gene CHS1 of four Candida species: *C. albicans,* 122 bp; *C. tropicalis,* 519 bp; *C. glabrata,* 535 bp; and *C. parapsilosis,* 311 bp. (Table 1) These amplified products were cloned into pCR Script SK(+) vectors and their DNA sequences were determined as described previously. The relative amplification efficiencies of these four products varied due to their size differences, making the assay more sensitive for detecting *C. albicans* as compared to the larger products generated by the other three Candida species. To change this situation the sequence information, generated from the four pCR-Script clones, was used in this study to create additional species-specific DNA primers and probes for four Candida species. These four primer pairs were so designed that each primer contained 45–55% GC and the amplified products that were generated were of similar sizes. This strategy was followed to ensure more equal amplification efficiencies of the various products to provide assays of similar sensitivities for all four Candida species.

Note that certain of the probes, *C. parapsilosis* and *C. glabrata,* of the parent application Ser. No. 08/120,780 used as one of the two primers along with a newly developed primer and probe in a PCR-based amplification assay detecting *C. parapsilosis* or *C. glabrata* with greater sensitivity for glabrata. The DNA sequence of each primer pair and corresponding probe and the sizes of the amplified products are set forth below.

The previously described primer pair from parent application Ser. No. 08/491,641 could not be used to amplify DNA from *C. krusei* (Table 1). Since this is also an important fungal pathogen, especially in immunosuppressed adults, it was important to have a species-specific primer pair for its amplification as well. To accomplish this, the primer pairs for *C. tropicalis, C. glabrata,* and *C. parapsilosis* described here were tested for their ability to generate an amplified product from *C. krusei* DNA. To achieve this, the annealing temperature of the PCR reactions was lowered from 60° C. to 40° C. to reduce the stringency and favor product formation. The PCR reaction mixtures containing the *C. krusei* DNA template and either the *C. glabrata* or *C. parapsilosis* primer pairs generated a 100 or 200 bp product, respectively. The amplified products from these two reactions were isolated separately on 4% NuSieve agarose gels (FMC BioProducts, Rockland, Me.) and purified with GeneClean Kit II (Bio 101, La Jolla, Calif.) for pCR-Script cloning and sequence determination, as described previously. The DNA sequence information obtained from the *C. krusei* clones was used to search the GenBank database for sequence similarities and to verify its identity with the CHS1 gene of *C. albicans* by using the Wisconsin GCG Sequence Analysis Software Package. The comparison revealed that the 100 and 200-bp products generated from *C. krusei* DNA template had the highest degree of homology to the *C. albicans* chitin synthase gene CHS1.

These probes can also be used to selectively quantitate these species in a variety of sample sources.

The newly designed probes and the primers along with those from the parent application for amplification of *C. albicans* used in their preparation are described below:

*Candida albicans* (See SEQ ID NOS:1, 2, and 3, respective)

CA-5' primers: 5'-CGC CTC TTG ATG GTG ATG AT-3'

CA-3' primers: 5'-TCC GGT ATC ACC TGG CTC-3'

CA Probe: 5'-CGT TCG TAC TAG AGT TGT GTT GTT TTG GAT-3'

*Candida parapsilosis* (See SEQ ID NOS:5, 7, and 8, respectively)

CP-5' primer: 5'-GAG GCT GTG ATG TGT GCT GTT GAC CAG-3' (orig. cp probe seq)

CP-3' primer: 5'-GAC AGC TAC GCA AAT CAA ACA G-3'

CP probe: 5'-GTC AAT TGC TGA CGA AAG TCA GCG-3'

*Candida tropicalis* (See SEQ ID NOS:9, 10, and 11, respectively)

CT-5'primer: 5'-CAG ACA GAC AGA CAG ACA GAC ACA C-3'

CT-3'primer: 5'-GAT CTG GAT ACT CTG TTC CAA GTC-3'

CT probe: 5'-GCG CGA GAA CGG GGA CAG AAA AAA TAC AC-3'

*Candida glabrata* (See SEQ ID NOS:4, 12, and 13, respectively)

CG-5' primer: 5'-CGA CTG GTT GAC GAT AAT CAG AGG AGA TGG G-3' (Orig. CG probe seq)

CG-3' primer: 5'-GTG CAG ATA TGT CGC TAT TAC CTT TGG-3'

CG probe: 5'-GAC GGA CGA CCT GCT TCC GAT TCT CAT AGA-3'

*Candida krusei* (See SEQ ID NOS:14, 15, and 16, respectively)

CK-5' primer: 5'-GGT TGA CAC TTC GCA TAC-3'

CK-3' primer: 5'-CGT ATG TGA CCA GTG AC-3'

CK probe: 5'-GTA GGT TCG ACA AGG ATG A-3'

General PCR-Based Assay Format of the Invention for Detection of Candida Sp.

Initially, the double-stranded DNA genome of Candida is denatured in order to break the hydrogen bonds holding the double-stranded DNA together, resulting in two single strands of DNA. The two DNA primers are added along with the other PCR reagents needed for DNA amplification to occur resulting in two complementary strands of DNA products being made.

The oligonucleotides or primers of the parent application comprise the sequences 5'-CGC CTC TTG ATG GTG ATG AT-3' and 5'-TCC GGT ATC ACC TGG CTC-3'. The Candida species that are amplified using the primer set of the parent application include: *Candida albicans, Candida glabrata, Candida tropicalis,* and *Candida parapsilosis.* The Candida species that are amplified using the new primer sets of this application include: *Candida krusei, Candida glabrata, Candida tropicalis,* and *Candida parapsilosis.*

Diagnostic Protocol I

The method includes the steps of: i) collecting a blood sample from the patient; ii) separating out the plasma and the buffy coat layer fractions present in the blood sample; iii) enzymatically digesting non-yeast DNA present in the remaining fractions; iv) enzymatically digesting the cell wall of yeast present in the remaining fractions in order to release DNA present in the cells; v) extracting, precipitating and resuspending the DNA; vi) adding primers having the sequences described above to the resuspended DNA; vii) maintaining the primers and the resuspended DNA under conditions such that hybridization and amplification occur; and viii) comparing the length of the resulting double-stranded DNA products of step (vii) to a measured double-stranded DNA genome template obtained from *Candida albicans, Candida glabrata, Candida tropicalis, Candida parapsilosis,* and *Candida krusei* thereby determining the species of Candida causing the infection in said patient. Again, the species of Candida which may be detected is selected from the group consisting of: *Candida krusei, Candida albicans, Candida glabrata, Candida tropicalis,* and *Candida parapsilosis.*

Diagnostic Protocol II

Another method of diagnosing a species of Candida in a patient is by use of species-specific probes alone, without primer-directed amplification. This method may also be used to confirm the species of Candida detected by the above-method.

In particular, this second method includes: i) denaturing the double-stranded DNA products of step (viii) of the above-method; ii) immobilizing the resulting, denatured DNA to a membrane; iii) adding Candida species-specific probes labelled at their 3' end, to the linked, denatured DNA; iv) maintaining conditions sufficient for hybridization to occur between said denatured DNA and the probes; v) adding antibody against the label, wherein the antibody is conjugated to an enzyme; vi) adding substrate which is acted upon by the enzyme, thereby forming a measurable product; vii) measuring the product, said measurement being compared to known measurements for *Candida krusei, Candida albicans, Candida glabrata, Candida tropicalis,* and *Candida parapsilosis,* thereby diagnosing or confirming the species of Candida present in the patient. The probes may be labeled with digoxigenin-dUTP or a fluorescent dye, for example. Furthermore, the enzyme of step (v) may be alkaline phosphatase and the substrate of step (vi) may be Lumi Phos 450. Again, the species to be detected or confirmed is selected from the group consisting of: *Candida krusei, Candida albicans, Candida glabrata, Candida tropicalis,* and *Candida parapsilosis.*

In addition, it is recognized that other conventional labeling methods can be employed and that certain modifications to these protocols in light of the particular type of label selected may be necessary.

Kit Packaging

As a matter of convenience, the reagents employed in the present invention can be provided in a kit packaged combination with predetermined amounts of reagents for use in determining and/or quantitating candida species. For example, a kit can comprise in packaged combination with other reagents any or all of primers or probes described above depending on need. Generally, it is desirable to include the requisite number of probes and/or primers to afford identification of all of the candida species referred to above. The oligonucleotide probes can be labelled or bound to a support or can be provided with groups that permit the probe or primer to be subsequently labelled or bound to a support. The kit can further include in the packaged combination buffers, developing systems for the selected label, other necessary enzymes, nucleoside triphosphates and the like.

Additionally, the kit may optionally contain a denaturation solution, a hybridization buffer, a wash solution and a microwell plate. The microwell plate is usually coated with desired probes of interest. It is also envisioned that the kit contain a internal calibration standard. Currently used is a Strep-aviden (SA) coated microtiter well. DNA probes are not bound to the plate, but rather the biotin-labeled amplimer is captured onto the surface of an SA-coated microtiter plate. This ss DNA is then hybridized with the Digoxigenin-dUTP-labeled probe. The calibration standard is preferably present for quantitation purposes. Note some available equipment does not require an internal calibration standard. The particular candida species to be diagnosed and quantitated is selected from the group consisting of *Candida krusei, Candida albicans, Candida glabrata, Candida tropicalis,* and *Candida parapsilosis.* Accordingly, these probes would be included.

Quantitation of Candida DNA

Quantification of genomic Candida DNA can be achieved using quantitative nucleic acid amplification methods. There is precedence for the success of this approach already in the HIV literature. Using PCR, quantitation can be accomplished by comparisons with externally amplified standards (Holodny et al., 1991), limiting dilution (Zhang et al., 1991) or competitive PCR with internal standards (Scaddin et al., 1992). The latter test has been found to the superior method, provided that amplification efficiencies of the wild-type and deletion mutant DNAs are equal (Nedelman et al., 1992).

Quantitation of Candida DNA would be based on co-amplification of an internal standard, using a dilution series. To achieve a quantitative assay with a dynamic working range of 5 logs, requires at least 6 amplification reactions per clinical specimen (this is the dilution series). This series would consist of one positive wild-type control with no added deletion mutant, and 5 reactions containing the wild-type control with increasing amounts of the deletion mutant (this is the internal standard). The amount of initial Candida genome can then be calculated from the ratio of wild-type signal to that of the deletion mutant signal.

For the disclosed system specifically, 5 deletion mutants will have to be created. Here one would strive for an internal deletion of 30–50 bases in length. The following are general guidelines that must be taken into consideration for generating a deletion mutant for an internal standard for quantitative PCR: 1) the deletion cannot be significantly smaller from the wild-type product to avoid creating an advantage for amplification of the significantly smaller mutant; 2) the two amplified products need to be different enough in size so that they are discernable from one another on an agarose gel; and 3) a deletion at either termini cannot be created because the same primer pair must be used for both the wild-type and deletion templates.

Since the entire DNA sequence of each of the "amplimers" is known, the DNA restriction sites are also known for each of these cloned templates. A suitable restriction site is chosen, and that specific restriction enzyme used to digest the DNA template (in this case its the sequencing plasmid that contains the amplified Candida DNA). The linear plasmid, minus the small insert, is then separated from the small DNA insert by gel purification and the former is relegated to form a circular plasmid. This deletion mutant is now used as the internal standard along with the wild type template for quantitation of the latter.

The newest quantitative approach is the realtime PCR amplification using fluorescent-labeled probes using the newest ABI TagMan system; ABI Prism 7700 Sequence Detection System by Perkin-Elmer.

Drug Resistance Determination

Current methods for determining drug resistance rely on in vitro susceptibility testing. However, this approach is time consuming and inconsistent. Newer, more rapid for monitoring patient response to treatment would aid in the management of the patient and would help to reduce morbidity and mortality. PCR has been used to monitor therapeutic efficacy in HIV infection as well as parasitic infections such as malaria.

This approach has been shown to correlate well in treatment of patients with malaria. Those patients unable to clear the organism from their bloodstream in less than 3 days represented a treatment failure and had to be switched to a different anti-malarial drug regimen (Kain et al., 1994). This PCR based test could also be used to monitor daily levels of Candida DNA to look for the clearance of the organism from the blood of a patient infected with Candida.

Based on the results from these protocols, the clinician can determine the optimal anti-fungal agent and its dosage. The regimen can be adjusted and tailored over time to employ the optimal amount of agent. Excess and excessive use of anti-fungal agents can be avoided in this manner.

Lane 1: DNA from *Candida albicans*
Lane 2: DNA from *Candida parapsilosis*
Lane 3: DNA from *Candida tropicalis*
Lane 4: DNA from *Candida glabrata*
Lane 5: No DNA (negative control)
Lane 6: molecular weight marker DNA.

Figure 2:
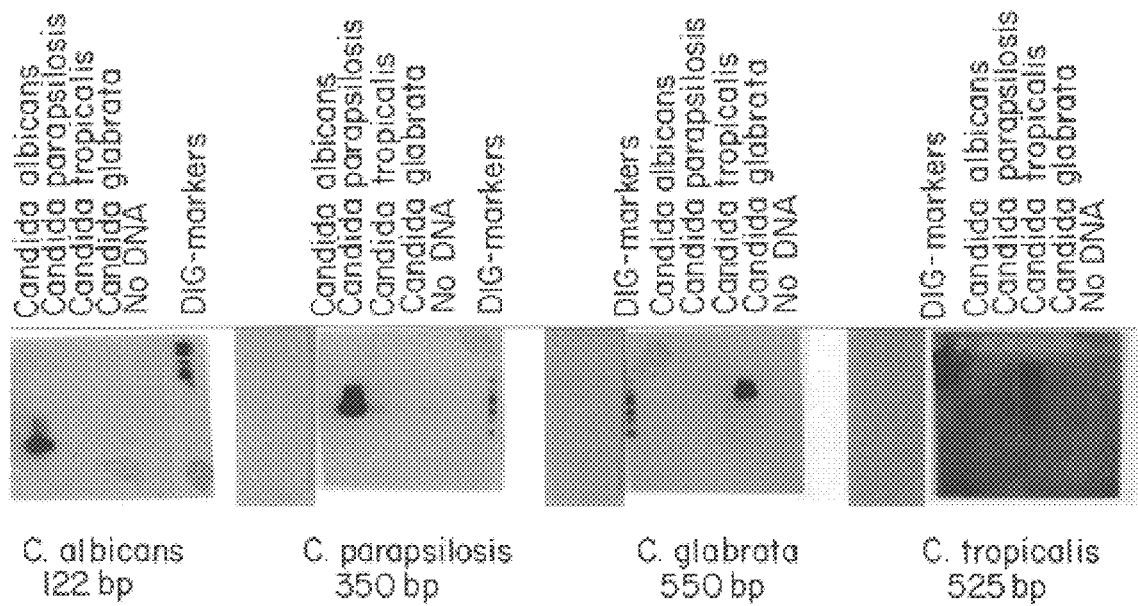

FIG. 2 represents four species-specific DNA probes disclosed in the parent application and used for the identification and confirmation of PCR amplified products from *Candida albicans, Candida glabrata, Candida parapsilosis,* and *Candida tropicalis.*

Figure 3A:
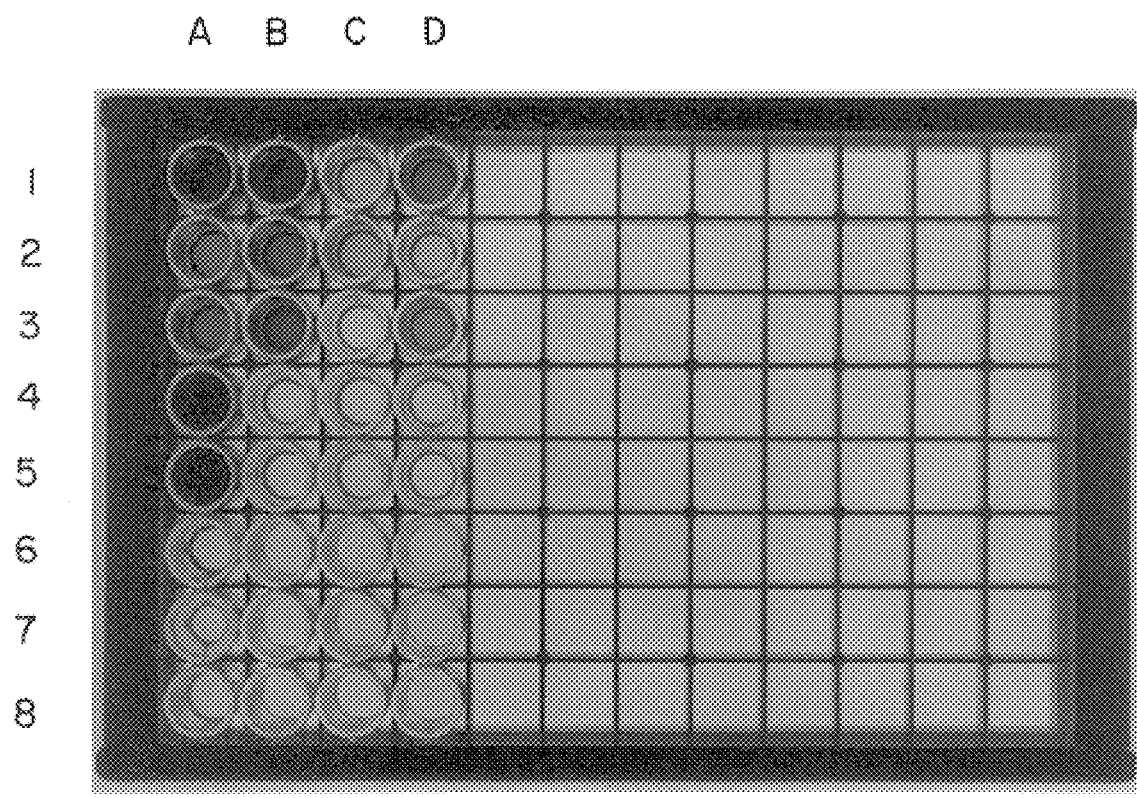
Figure 3B:
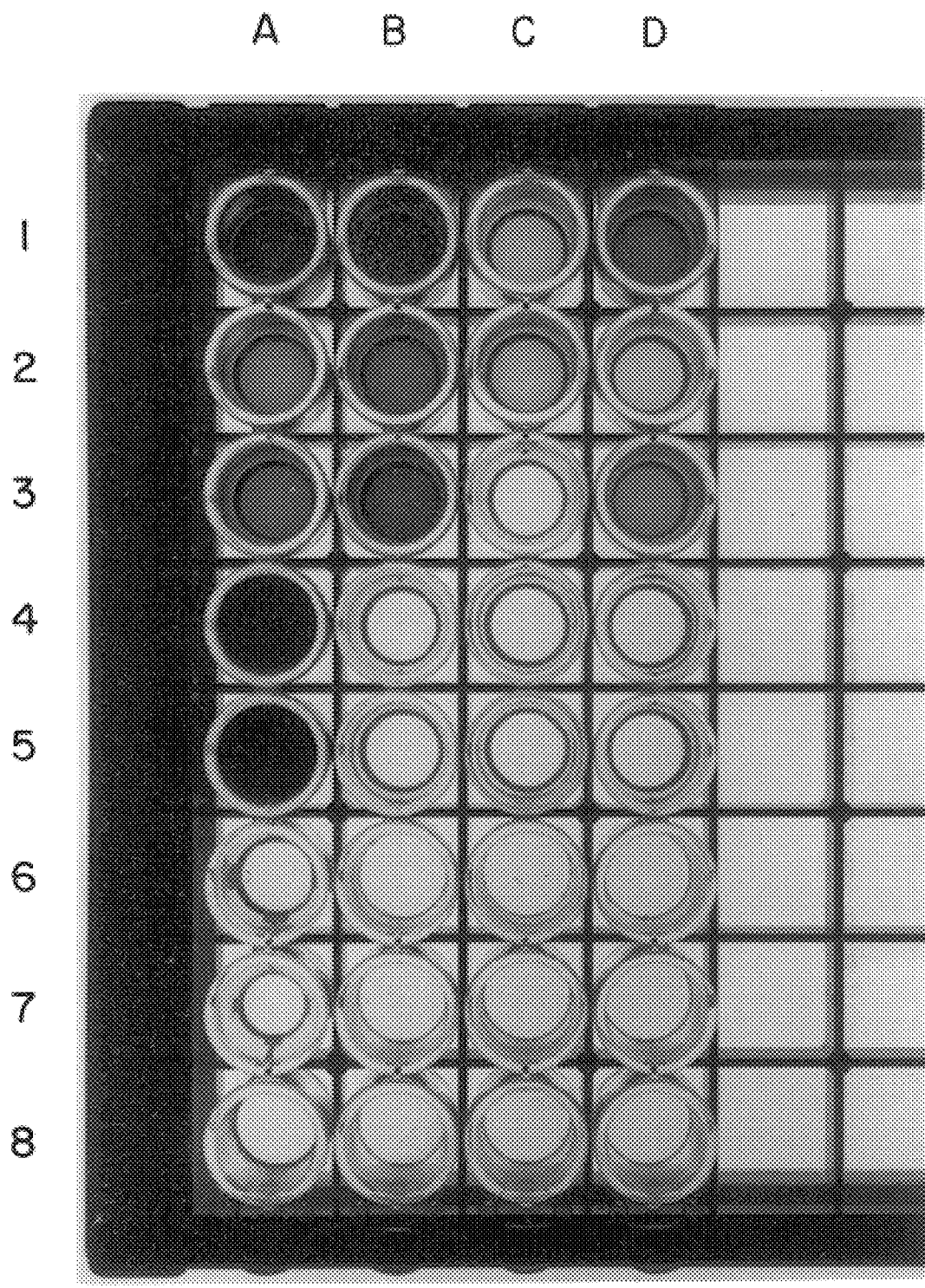

FIGS. 3A an 3B illustrate a plate showing the experimental results of Example VI. FIG. 3A and FIG. 3B are identical in content. FIG. 3B is an enlargement of FIG. 3A.

Figure 4:
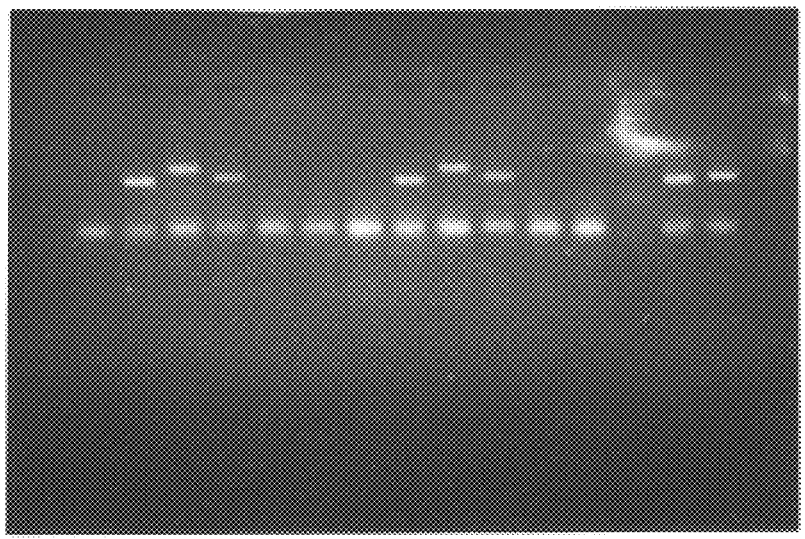

Column A1–A7—*C. albicans* probe
  (A1–A5)—*C. albicans* DNA
  (A6–A7)—No DNA
Column B1–B5—*C. parapsilosis* probe
  (B1–B3)—*C. parapsilosis* DNA
  (B4–B5)—No DNA
Column C1–C5—*C. tropicalis* probe
  (C1–C3)—*C. tropicalis* DNA
  (C4–C5)—No DNA
Column D1–D5—*C. glabrata* probe
  (D1–D3)—*C. glabrata* DNA
  (D4–D5)—No DNA FIG. 4: Multiplex PCR amplification and agarose gel electrophoretic detection of the three non-albican amplified products.

(From left to right in direction)

| Lane # | Genomic template amplified |
| --- | --- |
| Lanes 1 & 7: | C. albicans |
| Lanes 2 & 8: | C. parapsilosis |
| Lanes 3 & 9: | C. tropicalis |
| Lanes 4 & 10: | C. glabrata |
| Lanes 5 & 11: | Neg. co., No DNA |
| Lanes 6 & 12: | C. krusei |
| Lane 13: | Molecular weight markers |
| Lane 14: | Skip a lane |
| Lanes 15 & 16: | Ignore for the purposes of this figure |

Figure 5:
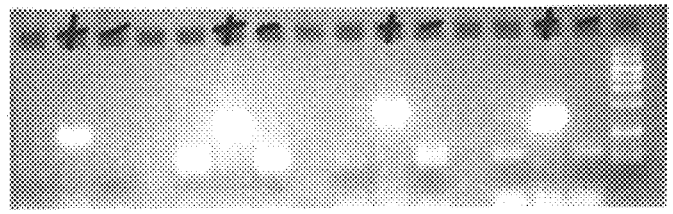

FIG. 5: PCR amplification and agarose gel electrophoretic detection of C. glabrata DNA from the blood of a patient with culture-proven candidiasis
(From left to right in direction)

| Lane # primers | DNA template added | Species-specific |
| --- | --- | --- |
| Lane 1 | Patient | C. albicans |
| Lane 2 | C. albicans | C. albicans |
| Lane 3 | No DNA | C. albicans |
| Lane 4 | SKIP LANE | |
| Lane 5 | Patient | C. parapsilosis |
| Lane 6 | C. parapsilosis | C. parapsilosis |
| Lane 7 | No DNA | C. parapsilosis |
| Lane 8 | SKIP LANE | |
| Lane 9 | Patient | C. tropicalis |
| Lane 10 | C. tropicalis | C. tropicalis |
| Lane 11 | No DNA | C. tropicalis |
| Lane 12 | SKIP LANE | |
| Lane 13 | Patient | C. glabrata |
| Lane 14 | C. glabrata | C. glabrata |
| Lane 15 | No DNA | C. glabrata |
| Lane 16 | Molecular weight marker only | |

DETAILED DESCRIPTION OF THE INVENTION

The Chitin synthase (CHS1) gene was selected for PCR amplification for the following reasons:

First, its gene product is clinically relevant, as it is the enzyme responsible for synthesizing chitin, the major cell wall component found in yeast, and the enzyme is upregulated in the filamentous pseudohyphae, the structure involved in tissue invasion. Braun and Calderone reported that chitin synthase levels are twofold higher from the filamentous phase of Candida albicans as compared to its yeast phase (J. Bacteriol 133:1472–77 (1978)).

Secondly, the chitin synthase gene is yeast-specific, having no mammalian, bacterial, or viral counterpart. This is an important point in avoiding false positive amplification of mammalian DNA which will be present in these clinical samples. More specifically, patients' blood samples contain nucleated cells, a source of a person's own DNA. Thus, this DNA will be co-extracted with yeast DNA during sample preparation for PCR analysis. Consequently, one does not want to amplify a yeast gene that has a mammalian homolog such as beta-actin, since one cannot separate mammalian DNA from "infectious" DNA.

Figure 1:
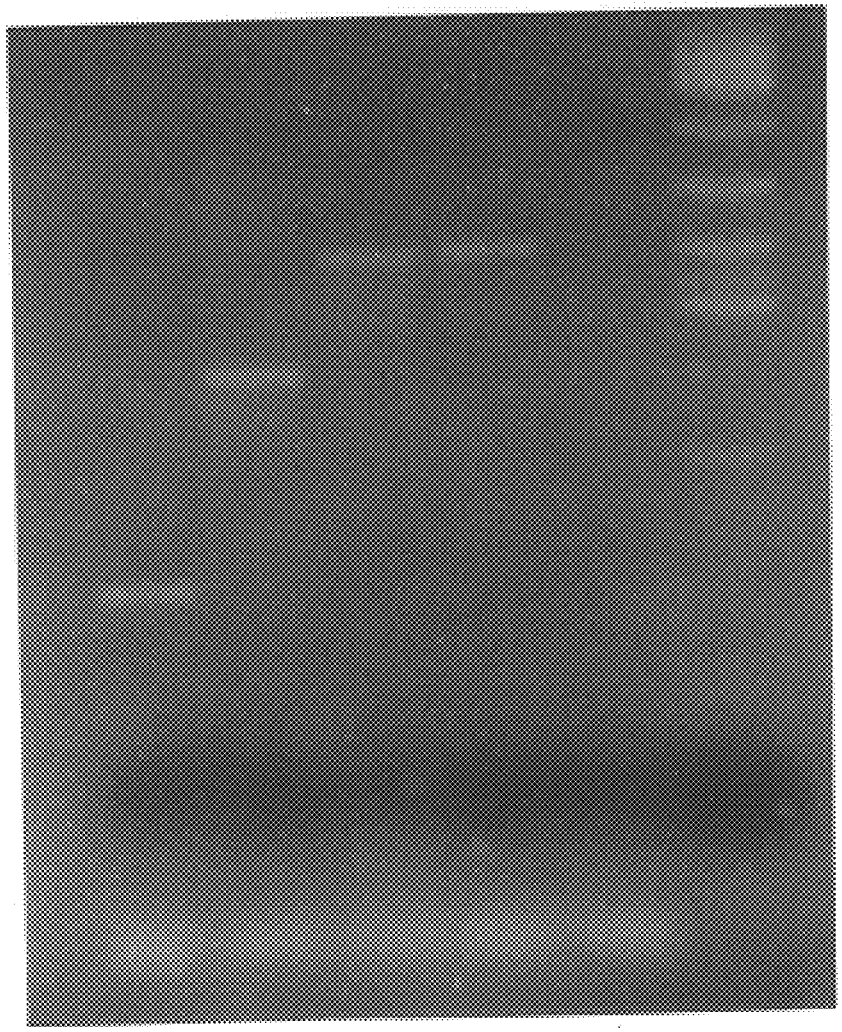
FIG. 1 represents PCR amplification of four Candida species using one primer pair disclosed in the parent application.

Finally, the region within the CHS1 gene selected for amplification contains no homology to Saccharomyces cerevisiae, the common bakers' and brewers' yeast, and the organism used to initially clone its homolog from Candida albicans. Based on this rationale, a set of primers was designed from sequence information provided by Au-Young (Mol. Microbiol. 4:197–207 (1990)) to amplify a 122 base pair product of the Candida albicans chitin synthase 1 gene. In further testing, this primer pair was successfully used to amplify DNA templates of Candida glabrata, Candida parapsilosis, and Candida tropicalis as well (FIG. 1). The four species represent over 95% of all neonatal infections caused by Candida.

In constructing a set of primers for PCR amplification, one primer must hybridize to one strand of DNA, and the other must hybridize to the opposite strand. The terms "coding" and "noncoding" (see below) come from the fact that the "coding" strand of DNA is read by the RNA polymerase during transcription to make messenger RNA. The "noncoding" strand of DNA is not "transcribed" by RNA polymerase. In other words, it does not code for a messenger RNA or a protein. It is the complement of the coding strand.

The sequences of the primer pair used in the parent application are as follows (see SEQ ID NOS:1 and 2, respectively):
Common Primers:
Coding (base pair #2039–2058):

5'-CGC CTC TTG ATG GTG ATG AT-3'.

Noncoding (base pair #2161–2143):

5'-TCC GGT ATC ACC TGG CTC-3'.

These primers do not amplify DNA purified from Candida krusei, Candida guilermondii, Candida lusitaniea, Saccharomyces cerevisiae, Escherichia coli, Klebsiella pneumoniae, Pseudomonas aeruginosa, Staphylococcus aureus, Beta-hemolytic Streptococcus group A and B, Streptococcus faecalis, Haemophilus influenza, Staphylococcus epidermidis, Neisseria gonorrhoeae, and Bacillus fragilis (see Table 1). These results indicate that the PCR primer pair used for DNA amplification demonstrates a good level of specificity.

TABLE 1

THE RESULTS OF INITIAL CHSI PRIMER PAIR
(PARENT APPLICATION NO. 08/491,641)
DRIVEN PCR AMPLIFICATION OF PURIFIED DNA

| DNA SOURCE | PCR PRODUCT SIZE (bp)[1] |
| --- | --- |
| Candida albicans | 122 |
| Candida glabrata | 550 (535) |
| Candida parapsilosis | 350 (311) |
| Candida tropicalis | 525 (519) |
| Candida krusei | no product generated (np) |
| Candida guilliermondii | np |
| Candida lusitaniae | np |
| Saccharomyces cerevisiae | np |
| Escherichia coli | np |
| Klebsiella pneumoniae | np |
| Pseudomonas aeruginosa | np |
| Haemophilus influenza | np |
| Neisseria gonorrhoeae | np |
| Bacteroides fragilis | np |
| Staphylococcus aureus | np |
| Staphylococcus epidermidis | np |
| Beta-hemolytic Streptococcus Group A | np |
| Beta-hemolytic Streptococcus Group B | np |
| Streptococcus faecalis | np |

[1]The parenthetical numeric values were determined based on sequencing work.

Using the above set of primers (i.e., 5'-CGC CTC TTG ATG GTG ATG AT-3' and 5'-TCC GGT ATC ACC TGG CTC3'), the PCR amplified products of the four Candida species were distinctly different in size from one another generating a species-specific fingerprint on an agarose gel. In order to determine whether various strains and clinical isolates of the same Candida species would consistently generate the same sized PCR amplified fragment, 44 different *Candida albicans* isolates, 25 *Candida glabrata* isolates, 20 *Candida tropicalis* isolates, and 19 *Candida parapsilosis* isolates were tested. In every case, the purified DNA from each isolate of the same species generated an identically-sized product after PCR amplification as the American Type Culture Collection (ATCC) strain. Therefore, this CHS1 primer pair is ideally suited to be used to consistently amplify and speciate the four major clinically relevant Candida species in a single PCR assay.

Again, it is important to note that this one set of primers will amplify DNA from *C. albicans, C. glabrata, C. parapsilosis,* and *C. tropicalis*. The PCR amplified DNAs are all different in size even though the same primer is used for the four different species. If the concentration of DNA is high enough, after PCR amplification, visible bands are seen on an ethidium-stained agarose gel. The sizes of the DNA fragments are compared to positive controls for each yeast species run on the same gel. As a confirmation, and for those samples where the DNA concentration is below a certain amount and not visible, the DNA from these gels can be transferred to membranes (referred to as Southern blotting technique) and hybridized with a species-specific DNA probe to visualize the amplified product.

The published sequence of the *Candida albicans* CHS1 was also used in designing a DNA probe for detection and confirmation of the *Candida albicans* PCR amplified product. This probe, recognized the 122 base pair fragment amplified from *Candida albicans* DNA but did not hybridize to amplified DNA generated from *Candida glabrata, Candida parapsilosis,* or *Candida tropicalis* templates (FIG. 2). Therefore, additional probes were required to provide an assay with similar levels of sensitivity as for *Candida albicans*.

To avoid false-positive signals, the DNA probes designed to be used for hybridization with PCR generated products need to lack any sequence homology with the primer pair used in the amplification assay. Thus, sequences internal to the two primers were utilized to design the initial probe. A probe of approximately 30 bases in length, under stringent hybridization conditions, ensures a good level of specificity.

As noted above, the initial probe did not recognize *C. glabrata, C. tropicalis* or *C. parapsilosis* amplified DNA. Thus, these amplified DNAs were run on a gel, the product was cut out of the gel, and the DNA was purified. This purified DNA was subsequently sequenced using the dideoxy nucleotide sequencing method. Determining this sequence information made it possible to: 1) create a species-specific probe and to 2) compare its sequence to DNA sequences within Genebank to look for homologous genes. This was done for all non-albicans species discussed in this application in order to determine that the "closest" fit in terms of DNA homology to pre-existing sequences in Genebank. The DNA sequences from the above noted 3 species gave closest homology to the chitin synthase 1 gene of *Candida albicans*. This is substantial evidence to indicate that the two primers are indeed amplifying the homologous CHS1 gene in *C. glabrata, C. parapsilosis* and *C. tropicalis*.

The sequences of the four species-specific probes disclosed in the parent application are as follows:

Species-Specific Probes:

*Candida albicans* (See SEQ ID NO:3): (base pair #2070–2099)

5'-CGT TCG TAC TAG AGT TGT GTT GTT TTG GAT-3'

*Candida glabrata* (See SEQ ID NO:4):

5'-CGA CTG GTT GAC GAT AAT CAG AGG AGA TGG G-3'

*Candida parapsilosis* (See SEQ ID NO:5):

5'-GAG GCT GTG ATG TGT GCT GTT GAC CAG-3'

*Candida tropicalis* (See SEQ ID NO:6):

5'-AGG CTT GCT CTT TGT CGG GCG AGC GAA CG-3'.

All of the probes confirm the specificity of the PCR product.

These probes are very useful for the study of the CHS1 gene in other Candida species at a basic scientific level with respect to, for example, gene expression and regulation as well as enzyme structure and regulation.

The method of using the primers and the probes will be described, in detail, below. However, basically, when the primers are utilized for diagnostic purposes:

Sample, e.g. blood, is collected from the patient and centrifuged in order to separate the blood into 3 layers (i.e., the red blood cells, the buffy coat and the plasma). The plasma and the buffy coat layer are then collected and treated with a detergent. The resulting product is then treated with, for example, an enzyme such as DNase I, in order to digest any non-yeast DNA which may be present. The chitin cell wall of the yeast is then digested, using Zymolase, for example, in order to release the yeast DNA for analysis. The DNA is then freed from bound protein by using, for example, Proteinase K digestion followed by detergent treatment.

The DNA is then extracted by using phenol, for example, and then precipitated by using a chemical such as ethanol, for example. Subsequently, the DNA pellet is resuspended in sterile distilled water. One is then ready to analyze the sample using the primers.

In particular, a portion (e.g., 1 μl) of the sample is added to a PCR master mix (e.g., 49 μl). The mix contains both primers as well as deoxynucleotides (i.e., DATP, dCTP, dGTP, and dTTP, or dUTP), and for example, buffer, magnesium chloride, and Taq polymerase. Several cycles of PCR amplification, e.g., 30 or 40, are carried out. First the DNA must be denatured, e.g., at 94° C. for 1 min., the primers must anneal, e.g., at 55° C. for 2 min., and elongation and DNA synthesis must be allowed to occur, e.g., at 72° C. for 1 min.

After the DNA-yeast-specific product is made, it is then analyzed on agarose gel or detected in a plate-based assay as described.

It should also be noted that all of the PCR "runs" contain 4 positive controls (i.e., one each of *C. albicans, C. parapsilosis, C. tropicalis,* and *C. glabrata* template DNA (see FIG. 1)). Several negative controls are also run. No DNA is added to these tubes, so no DNA product should be made. In addition, digoxigenin-labeled DNA molecular weight standards are run along side the clinical samples and controls on the agarose gel as a molecular weight marker to estimate the sizes of the DNA fragments that were generated by PCR.

In order to utilize the probes for diagnostic and confirmatory purposes, the following steps are carried out:

The DNA product separated onto an agarose gel is denatured and blotted onto a nylon membrane where it is permanently linked. Samples are then run in quadruplicate so that all four probes can be analyzed individually.

This denatured DNA exists as single-stranded DNA and is available to hydrogen bond (i.e., hybridize) to a single-stranded DNA probe.

Species-specific probes are then used individually. These DNA probes are 3' tail-labelled with, for example, a digoxigenin labeled dUTP, using $T_4$ terminal transferase, for example. The labeled probes are then added to the DNA-containing blots and, subsequently, the following reagents are added: antibody to digoxigenin (or label utilized) which is conjugated to an enzyme, for example, alkaline phosphatase.

Substrate is then added which the enzyme converts to a measurable product. The substrate may be Lumi Phos 450 which emits light that is detected if a piece of X-ray film is put down on the blot for approximately 10–20 minutes. The X-ray film is then developed to give a signal (see FIG. 2).

These probes are used for confirmation purposes, and provide evidence that the "correct" sized PCR product is also yeast species specific. The use of DNA probes also provides a much more sensitive assay, as this assay will detect a product which is not visible upon ethidium bromide staining of the agarose gel.

It is to be recognized that the use of other conventional labels, markers can be used.

For example, the presence of bound detectable marker can be detected using various conventional methods, e.g., fluorimetry, autoradiography, spectrophotometric, enzymatic or immunological methods.

The protocols used are illustrated by the use of the following examples:

EXAMPLE I

Specimen Amplification

Specimen Processing:

Ethylenediaminetetraacetic (EDTA) containing whole blood samples were processed in a manner similar to that described by Buchman et al. (Surgery 108:338–47 (1990)). Briefly, 100 $\mu$l to 1 ml volumes of EDTA containing whole blood was collected by venipuncture or obtained from central lines of patients with culture proven Candidiasis. These blood samples were collected as soon as possible after the blood cultures became positive with yeast. The red cells in the specimens were pelleted by centrifugation (2 min at 13,000×g), and the combined plasma and buffy coat fractions collected. The fractions were treated with an equal volume of a non-ionic detergent cocktail containing 1% Tween-20 and 1% NP-40 dissolved in 50 mM TRIS buffer pH 7.5. After centrifugation (13,000×g for 2 min), the pellets were resuspended in a non-ionic detergent cocktail containing 0.5% Tween-20 and 0.5% NP-40 in 50 mM TRIS buffer pH 7.5. The resulting pellets were washed twice in 50 mM TRIS buffer pH 7.5 containing 10 mM MgCl and treated with DNase I at a concentration of 10 mg/ml for 15 minutes at 37° C. The DNase I enzyme was subsequently inactivated by adding EDTA to a final concentration of 10 mM and heating to 85° C. for 30 minutes. Any yeast cells present within the samples were pelleted by centrifugation at 13,000×g for 10 min., and their cell walls digested using a yeast digestion buffer consisting of 300 mg/ml Zymolase or yeast lytic enzyme in 50 mM TRIS buffer pH 7.5 containing 10 mM EDTA and 28 mM Beta-mercaptoethanol. Specimens were incubated for 1–2 hours at 37° C. before adding sodium dodecyl sulfate (SDS) and Proteinase-K (PK) to final concentrations of 0.1% and 15 mg/ml respectively. The samples were incubated for 5 minutes at 37° C. before being boiled for 5 minutes, quick chilled, and the DNA extracted once in an equal volume of buffer saturated phenol and chloroform/isoamyl alcohol (24:1), once with an equal volume of chloroform-isoamyl alcohol alone and finally precipitated in 2.5 volumes of 100% ethanol.

Each DNA pellet was resuspended in 25 ul sterile $dH_2O$ and a 1 ul sample amplified by PCR.

Preparation of Control DNA:

Single colonies of the ATCC strains of *Candida albicans, Candida glabrata, Candida parapsilosis,* and *Candida tropicalis* were inoculated into 1 ml broth cultures of brain heart infusion and incubated at 37° C. for 24–28 hours. The cultures were then centrifuged for 2 mins. at 13,000×g to pellet the yeast. These pellets were resuspended in 100 $\mu$l volumes of 50 mM TRIS HCl pH 7.5 containing 10 mM EDTA and 28 mM Beta-mercaptoethanol containing 300 $\mu$g/ml of the yeast lytic enzyme Zymolase. Samples were incubated at 37° C. for 1 hr. to prepare spheroplasts. The spheroplasts were solubilized by adding SDS and PK to final concentrations of 0.1% and 15 $\mu$g/ml, respectively for 5 min. at 37° C., and then boiled for 5 mins. at 95° C. to inactivate the PK. Samples were quick chilled on ice and the DNA extracted using equal volumes of buffer saturated phenol and chloroform isoamyl alcohol (24:1) and once in an equal volume of chloroform isoamyl alcohol alone. The nucleic acid within the aqueous phase of the samples was precipitated with the addition of one-half volume 7.5M ammonium acetate and 3 volumes of ice cold 100% ethanol following 30 min. at −80° C. and pelleted by centrifugation at 13,000×g for 15 mins. at 4° C. The resulting DNA pellets were washed in ice cold 70% ethanol and resuspended in 25 $\mu$l of sterile distilled water prior to amplification.

PCR Amplification Strategy:

Each reaction for PCR amplification contained 1 $\mu$l of extracted DNA template from clinical samples or control organisms and 49 $\mu$l of the following PCR master mix: 5 $\mu$l of a 10× PCR buffer containing 20 mM magnesium chloride, 8 $\mu$l of a 200 $\mu$M deoxynucleotide triphosphate (DNTP or dUTP) mixture (equimolar amounts of DATP, dCTP, dGTP and dTTP or dUTP), 1 $\mu$l of a 20 mM stock of each CHS1 primer, and 1.25 Units of AmpliTaq polymerase. Large batches of the PCR master mix containing the TRIS buffer, magnesium chloride, dNTPs and primers (excluding the AmpliTaq polymerase) were stored in small individual use aliquots at −20° C., thawed, used once and then discarded. This procedure helps prevent contamination problems as well as assay consistency problems. Positive displacement pipettes were used in preparing and aliquoting the PCR master mix and when adding the clinical sample to the reaction mixture. A 50 $\mu$l overlay was then added to each tube before placing them in the 480 Series Perkin-Elmer Cetus thermocycler. Thirty cycles of a three-step amplification process were run including 94° C. for 1 min., 54° C. for 2 mins. and 72° C. for 1 min; followed by 7 mins. extension time at 72°C. to complete the assay. Twenty microliters of each sample were analyzed in quadruplicate on a 1% LE agarose/3% NuSieve agarose gel in 1× TAE buffer. Each batch of samples analyzed must also include the four positive control DNA templates and negative control samples (tubes lacking template DNA). The agarose gel containing the amplified DNA is then treated with 0.4M sodium hydroxide and 0.6M sodium chloride for 30 mins. to obtain single stranded DNA for overnight transfer to a nylon membrane (Gene Screen Plus, Dupont) in the same denaturing solution.

On the next day, the nylon membrane was neutralized in 0.5M TRIS-HCl, pH 7.0 and 1M sodium chloride for 15 mins. before the DNA was UV-crosslinked onto the membrane in preparation for hybridization with the 4 species-specific probes: one for *C. albicans, C. glabrata, C. parapsilosis,* and *C. tropicalis.*

EXAMPLE II

Detection of PCR Amplified DNA Products Using Species-Specific Probes Labelled with Digoxigenin Linked dUTP In addition to the probe designed from the published sequence of *C. albicans*, three probes were designed after the entire sequence of each PCR amplified product was determined. The individual PCR generated fragments of *Candida albicans, Candida glabrata, Candida parapsilosis,* and *Candida tropicalis* were cloned into pCR-Script SK(+) vector using $T_4$ directed blunt end ligation (catalog #211190 Stratagene, LaJolla, Calif.). The flanking $T_3$ and $T_7$ promoters and related primers were used in conjunction with Sequenase Version 2.0 DNA sequencing kit to determine the sequence of the PCR inserts (USB, Cleveland, Ohio). As a result, four species-specific probes are available to provide maximal sensitivity for detecting *Candida albicans, Candida glabrata, Candida parapsilosis,* and *Candida tropicalis* using a single primer pair.

Each species-specific DNA probe is 3' tail-labeled with digoxigenin-dUTP (DIG-dUTP) using the enzyme Terminal Transferase according to the manufacturer's directions (Boehringer Mannheim).

In terms of sensitivity, the PCR assay, in conjunction with Southern blot analysis using digoxigenin-dUTP labeled probes and a chemiluminescent detection system, was able to detect between 10–100 colony forming units per milliliter (CFU/ml) of *Candida albicans*. This level of sensitivity was similar for the other three Candida species mentioned. The sensitivity of the assay was determined by adding known amounts (CFU/ml) of *Candida albicans* to 1 ml volumes of EDTA containing whole blood, and the DNA extracted from each sample was amplified and detected as described in Example I.

EXAMPLE III

A Retrospective Study Comparing PCR to Culture for Identifying Candida in Blood

In a retrospective study of 14 children or neonates with culture-proven candidemia, the PCR and culture results were identical in 24 of 25 blood samples tested (Table 2). In this study sample, volumes from between 0.2 to 1 ml of EDTA containing the whole blood was collected from neonates or children documented to have culture-proven candidemia. Twenty-four of the 25 blood samples analyzed by PCR were collected prior to initiation of anti-fungal therapy. However, in the one case in which the blood culture grew *Candida albicans* and the PCR results were negative, the blood sample for PCR analysis was not collected until after 5 days of amphotericin-B therapy. These results strongly suggest that this PCR-based assay permits both identification and speciation of the four major medically relevant Candida species in less time than conventional culturing. This high degree of correlation and decreased turnaround time for Candida identification using PCR instead of culture will be helpful in better assisting the clinician in diagnosing systemic candidiasis.

TABLE 2

| PATIENT | # OF BLOOD SAMPLES | CULTURE RESULTS | PCR RESULTS |
| --- | --- | --- | --- |
| 1 | 2 | C. albicans | C. albicans |
| 2 | 2 | C. albicans | C. albicans |
| 3 | 2 | C. albicans | C. albicans |
| 4 | 2 | C. albicans | C. albicans |
| 5 | 2 | C. albicans | C. albicans |
| 6 | 1 | C. albicans | Negative* |
| 7 | 2 | C. albicans | C. albicans |
| 8 | 2 | C. albicans | C. albicans |
| 9 | 1 | C. glabrata | C. glabrata |
| 10 | 2 | C. parapsilosis | C. parapsilosis |
| 11 | 2 | C. parapsilosis | C. parapsilosis |
| 12 | 1 | C. parapsilosis | C. parapsilosis |
| 13 | 2 | C. parapsilosis | C. parapsilosis |
| 14 | 2 | C. tropicalis | C. tropicalis |

*Blood sample for PCR analysis was taken 5 days after initiation of anti-fungal therapy.

EXAMPLE IV

Three Additional Approaches of Carrying Out Detection and/or Confirmation of the Four Species of Candida The four Candida probes cloned into pCR-Script vector also allow for the synthesis of RNA-based transcripts which can be used in another type of a detection system for PCR-generated DNA products. This detection process eliminates gel blots and involves the use of the enzyme linked immunosorbent assay (ELISA) assay and the Digene Diagnostic, Inc. system.

Approach 1:

The primer is labeled at the 5' end with biotin. All 4 Candida species PCR fragments are cloned into pCR-Script in order to generate RNA probes. Ninety-six well plates are coated with Strep-Avidin.

Biotinylated primer is incorporated into the PCR product. This double-stranded DNA is then denatured to give single strands, and the strands are hybridized to the species-specific RNA probe. This RNA/DNA (biotin) hybrid is "captured" by having a very high affinity for Strep-Avidin.

The specific RNA/DNA linked to Strep-Avidin is then recognized by an antibody which recognizes RNA/DNA based hybrids. This antibody is conjugated to alkaline phosphatase enzyme and is detected by addition of a calorimetric substrate.

Approach 2:

Reagents: Strep-Avidin coated 96 well plates, biotin labelled primer, digoxigenin-labeled probe, chemiluminescent substrate.

The amplified DNA product contains biotin. The PCR generated DNA is denatured to give single-stranded DNA. The denatured DNA hybridizes with the digoxigenin-labeled DNA probe (in quadruplicate (i.e., one reaction for each species-specific probe)). The $DNA_{(biotin)}/DNA_{(dig)}$ hybrid is added to the Strep-Avidin coated wells where the biotin labeled PCR generated DNA binds to the Strep-Avidin. An anti-digoxigenin antibody is added to the wells containing the bound $DNA_{(biotin)}/DNA_{(dig)}$ hybrid. The chemiluminescent substrate is added to react with the DIG/DIG antibody complex.

The DIG-labeled DNA probe alone does not bind to Strep-Avidin, so no false-positive reactions are obtained.

The biotin labeled primers alone can bind to the Strep-Avidin coated plates but do not cause a substrate change because the antibody conjugated enzyme is to digoxigenin not to biotin. Thus, no false-positive results are obtained.

Approach 3:

The detection system described hereinafter will replace the costly and time consuming agarose gel electrophoresis and Southern blot techniques for detecting the amplified products of Candida after PCR amplification.

For the PCR amplification process, primer $CHS1_{2039}$ (or one primer of each primer pair) is synthesized with a biotin tag on its 5' end. This biotinylated primer is incorporated into one strand of the double-stranded DNA product, and "captured" in a well of a Streptavidin coated microtiter plate. The double-stranded product is treated with 1.6% NaOH to dissociate the two strands, so that the unlabeled and unbound strand of DNA can be washed away, leaving only the single-stranded, biotin-labeled product bound to the plate. This product is now available (after neutralization of the NaOH) to hybridize with a species-specific oligonucleotide probe that is 3' tailed labeled with digoxigenin dUTP (Boehringer Mannheim Corp, DIG Oligonucleotide Tailing Kit; Cat. #1417 231). The presence of the captured, hybridized product is then detected with an alkaline phosphatase conjugated antidigoxigenin antibody (Boehringer Mannheim Corp., Cat. #1093 274) and visualized with the substrates; Nitro blue tetrazolium chloride (NBT) and 5-bromo-4-chloro-e-ndolyl-phosphate, 4-toluidine salt (X-phosphate, 4-toludine sale) (Boehringer Mannheim Corp., Cat. #1383 213 and Cat. #1383 221, respectively) and an ELISA amplification system (Gibco BRL Life Technologies, Inc., Cat. #19589-019). The principle of the amplification system is as follows. Each molecule of product from the first reaction (alkaline phosphatase) takes part in many cycles (i.e., another type of amplification) of the second reaction (NADH/NADPH redox reaction). This type of calorimetric system achieves a similar level of sensitivity to that found in the chemiluminescent system (Lumi-Phos), which is equally sensitive to a system that utilized a radio-labeled oligonucleotide probe. The optical density of each well in the plate is read at an absorbance value of 490 nm.

In summary, this approach includes the following steps:
1. During the PCR amplification process, the biotinylated primer is incorporated into the newly made DNA amplimer.
2. The entire double-stranded, biotinylated PCR product is captured within a strep-avidin coated well within a microtiter plate.
3. The captured, double-stranded DNA product is denatured using alkaline conditions. This enables the unlabeled strand of DNA to be washed away during a rinse step, leaving the captured single strand of DNA available for probe hybridization.
4. Hybridization buffer containing the single-stranded, 3'-digoxigenin-dUTP tail-labeled DNA probe is added to the wells containing the captured single-stranded amplimer. Hybridization of this probe with the biotin-labeled, single-stranded amplimer takes place at an elevated temperature inside a heated waterbath.
5. Excess probe, which is unhybridized, is washed away in a rinse step.
6. An appropriate concentration of the conjugated antibody; alkaline phosphatase conjugated anti-digoxigenin, is added to the wells of the microtiter plate.
7. An appropriate substrate is added to the wells, along with the amplifier system (NADP/NADPH).
8. The reaction is stopped upon addition of $H_2SO_4$.
9. The absorbance of each reaction is read at a wavelength of 490 on a spectrophotometer that is adapted to reading microtiter plates.

Following approach No. 3 using the new probes or using the probes of the parent application Ser. No. 08/120,780, the following results shown in the tables 3, 4, and 5 were achieved.

PCR Amplification of the Genomic DNA from 4 Medically Important Candida Species Using Four Individual Species-Specific Primer Pairs Genomic DNA extracts were prepared from overnight cultures of C. albicans, C. parapsilosis, C. tropicalis and C. glabrata as described previously. PCR amplification of each DNA template (1 ug) was performed using the newly designed species-specific primer pairs. Detection of the amplified products were achieved using our newly described microtiter plate-based assay. Briefly, each biotinylated amplimer was captured in streptavidin-coated wells, and after denaturation, was hybridized separately with each of the 4 species-specific probes. The amplified positive controls were the 4 pCR-Script SK(+) plasmids that contain the individual amplimers generated from a PCR-based assay using the original single primer pair: $CHS1_{2039}$ and $CHS1_{2143}$. The 4 negative controls that were amplified and tested in this plate-based assay lacked template DNA.

TABLE 3

Absorbance$_{490nm}$ readings obtained after PCR amplification of genomic DNA using the original CHS1 primer pair, and species-specific probes in a microtiter plate-based EIA.

| A | P | T | G | Neg. |
|---|---|---|---|------|
| 2.372 | 0.657 | 0.805 | 0.370 | 0.120 |

A = C. albicans
P = C. parapsilosis
T = C. tropicalis
G = C. glabrata
Neg. = Negative control; no DNA
A lower stringency annealing temperature; 54° C. was used in this PCR-based assay, identical to the conditions described in applicant's original article on the use of a single primer pair for amplifying 4 Candida species; J. Clin. Micro. 32:2962–7, 1994.

TABLE 4[2]

| | NEWLY DESIGNED DNA PROBES | | | | |
|---|---|---|---|---|---|
| | A | P | T | G | K |
| DNA TEMPLATE | | | | | |
| Ag | 1.901 | 0.052 | 0.104 | 0.068 | 0.022 |
| Pg | 0.262 | 1.494 | 0.126 | 0.094 | 0.024 |
| Tg | 0.327 | 0.072 | 1.592 | 0.117 | 0.032 |
| Gg | 0.100 | 0.052 | 0.105 | 1.860 | 0.054 |
| Kg | 0.080 | 0.082 | 0.099 | 0.099 | 2.032 |
| Neg. | 0.062 | 0.063 | 0.032 | 0.049 | 0.093 |
| Corresponding Plasmid + Controls | 1.425* | 1.810* | 1.531* | 1.727* | 2.276* | g= genomic DNA template
A = C. albicans
P = C. parapsilosis
T = C. tropicalis
G = C. glabrata
K = C. krusei
*= The corresponding positive-control plasmid DNA
Interpretation of the absorbance values:
Positive value = ≧0.400
Negative value = <0.350
Equivocal range = >0.350–0.399; assay must be repeated
[2]Molecular Diagnosis, Vol. 1, No. 1, pp. 1–8, (March,1996).

These preliminary results reveal the species-specific nature of both the primers and the probes for detecting and speciating the candida DNA. In this experiment, only the PCR master mix containing the species-specific primers and its corresponding DNA template gave a positive absorbance reading. All remaining template and primer combinations had negative absorbance values. A portion of each amplified reaction was also analyzed using agarose gel electrophoresis. The results again showed that only the reaction mixtures containing the species-specific primers and corresponding DNA template generated a DNA fragment, which was of the predicted size and which hybridized only to its species-specific probe.

From a comparison of Table 3 with Table 4, the enhanced efficiency of the newly designed primer pairs for amplifying the non-albicans genomic DNA can be appreciated, relative to the original primer pair.

In addition, the multiplexing of the non-albican primer sets to reduce effectively the number of amplification reactions that would have to be run on a clinical specimen for detecting these four medically important candida species. The data is shown in Table 5.

Multiplex PCR Amplification of Genomic DNA from 5 Medically Important Candida Species Unlike the original CHS1 primer pair that was shown to amplify the DNA from all four Candida species, these newly designed species-specific primer pairs amplify only the DNA from their respective Candida species, namely, *C. glabrata, C. parapsilosis, C. tropicalis* and *C. krusei.* Applicant found an advantage to this more complex system, that being a significant increase in the level of sensitivity for detecting the candidal organism (Table 4). This is important in detecting cases of candidemia, as the level of yeast in clinical specimens is often very low, at or below 100 colony forming units per milliliter of whole blood.

This amplification system could be used as described; one species-specific primer pair per PCR reaction mixture. However, it would be more advantageous economically to have more than one species-specific primer pair together in a single PCR reaction, which is why applicant proposed the multiplex PCR approach.

Clinical samples to be tested for candida DNA will rarely, if ever, contain more than one species. Therefore, this approach was designed not so much to detect and identify multiple Candida species within a single reaction, but to reduce the overall cost of the assay. This approach would eliminate having to set up 5 individual PCR reactions, and would instead, allow one to set up just 1 or 2 reactions. This would reduce significantly the cost of the test. Therefore, applicant has designed a system in which one PCR master mix would contain the primer pair for *C. albicans* and the second PCR master mix would contain the other 4 non-albican primers for amplifying *C. glabrata, C. parapsilosis, C. tropicalis,* or *C. krusei.*

Table 5 illustrates these species-specificities of each primer pair. Significant absorbences reading (490 nm) were seen only after amplification of the DNA template with its related primer pair, and with hybridization of this amplified DNA with its homologous probe (represented by the underlined values). One does not have to be concerned about generating false-positive signals for any of the non-albican species using the original CHS1 primer pair because a higher annealing temperature is used in these PCR amplification reactions to ensure high stringency; primer binding to homologous template only, and not that of *C. glabrata, C. parapsilosis* or *C. tropicalis* or *C. krusei.*

TABLE 5

MULTIPLEX PCR USING THE THREE
NEWLY DESIGNED DNA PRIMERS AND PROBES

| | A | P | T | G |
|---|---|---|---|---|
| DNA TEMPLATE | | | | |
| Ag | 0.057* | 0.064 | 0.068 | 0.083 |
| Pg | 0.052 | <u>1.976</u> | 0.084 | 0.077 |
| Tg | 0.056 | 0.096 | <u>1.263</u> | 0.092 |
| Gg | 0.057 | 0.093 | 0.091 | <u>1.877</u> |
| Neg. | 0.059 | 0.104 | 0.092 | 0.095 |
| Corresponding Plasmid + Controls | 0.057* | >3.000 | >3.000 | 2.810 | g= genomic DNA was amplified by PCR for this detection assay.
*= NOTE: This PCR amplification mix does not contain the *C. albican* primers, CHS1$_{2039}$ and CHS1$_{2143}$, so PCR amplification of C.A. template should not and does not occur.

EXAMPLE V

Modification of Clinical Specimen Processing

In order to shorten sample processing time, zirconium beads may be added to the plasma/buffy coat layer, and the mixture is "beat-up" on the Microbead beater (Biospec Products) for three 2 minute cycles. The beads are then pelleted, and the released yeast DNA (from the fluid-containing broken yeast cell) is phenol extracted, EtOH precipitated, and a microliter volume is PCR amplified as described above. This modification eliminates detergent treatment, DNAase and Zymolase treatment. It is quicker to perform than the basic sample preparation.

EXAMPLE VI

Microtiter Plate-Based Detection of Amplified Products

Equal amounts of the 4 species of candida (genomic templates) were amplified individually using the original (parent application) primer pair as described above. Equal volumes of the biotin-labeled, amplified products were captured on Streptavidin-coated plates and hybridized with their respective probes, following the protocol for the newly described microtiter plate-based assay.

Results: FIG. 3 illustrates a microtiter plate where a deep red color is indicative of a positive result, no color development (clear) is indicative of a negative result. This picture was not specifically set up for comparison between candida species for amplification efficiencies, although it can be seen that the wells containing *C. albicans* DNA are more intensely red than non-albican containing wells when the consensus primer pair is used.

EXAMPLE VII

Multiplex PCR Amplification and Agarose Gel Electrophoretic Detection of the Three Non-albican Amplified Products Purified yeast DNA was extracted by a method previously described in this application. One microliter of DNA extract (1 ug) was added to 49 ul of a PCR master mix containing an equal concentration (0.25 uM or 0.5 uM) of all 3 newly described species-specific primers for *C. parapsilosis, C. tropicalis* and *C. glabrata.* Forty cycles of amplification were carried out as previously described. Twenty-five microlitres of each of the amplified products were analyzed on a 3% NuSieve/1% LE agarose gel for the presence of the predicted fragments. Lanes 1–6 contain 0.25 uM of each of the 3 non-albicans primers. Lanes 7–12 contain 0.5 uM of each of the 3 non-albican primers. The predicted sizes for the newly designed species specific DNA amplimers are as follows: C. parapsilosis; 148 bp. C. tropicalis; 183 bp, and C. glabrata; 156 bp.

Results: Use of the PCR master mix containing all 3 newly designed species-specific primer pairs resulted in accurate amplification of the predicted sized fragment for the DNA template added. No aberrant bands were seen on the gel as a result of any non-specific amplification. Therefore, the multiplex approach to DNA amplification was successful and products were generated with C. parapsilosis, C. tropicalis, C. glabrata, C. albicans and C. krusei DNA templates, therefore providing template specificity. The results are shown in FIG. 4.

EXAMPLE VIII

PCR Amplification and Agarose Gel Electrophoretic Detection of C. glabrata DNA from the Blood of a Patient With Culture-Proven Candidiasis DNA was extracted using a method previously described, from a 100 ul sample of plasma from a patient with culture-proven candidiasis. One ul volumes of the purified DNA from the patient was added to 49 ul of PCR master mixes containing one of four, individual species-specific primer pairs. The 4 positive control DNAs consisted of 1 ug of purified genomic DNA extracted from overnight cultures. After 40 cycles of amplification, 25 µl volumes of each amplified product was analyzed on a 3% NuSieve/1% LE agarose composite gel, containing ethidium bromide for DNA visualization.

Results: Analysis of the PCR-amplified product from the patient revealed a DNA fragment of the same size as that generated by the C. glabrata positive control template in Lane 13 in which C. glabrata primers were included in the PCR master mix. The patients sample did not generate any other DNA fragment when added to any of the other 3 PCR master mixes. Therefore, the patient's blood was found to contain C. glabrata DNA. The results are shown in FIG. 5.

TABLE 6

PCR BASED AMPLIFICATION AND DETECTION OF A CLINICAL BLOOD SAMPLE USING THE NEWLY DESIGNED PRIMER PAIRS AND PROBES DNA PRIMERS AND PROBES

|  | A | P | T | G |
|---|---|---|---|---|
| DNA TEMPLATE |  |  |  |  |
| JW^ | 0.071 | 0.116 | 0.133 | 0.350 |
| Neg. | 0.059 | 0.104 | 0.092 | 0.095 |
| Corresponding Plasmid + Controls | 2.870 | >3.000 | >3.000 | 2.810 |

^ = Patient blood sample from JW
Test interpretation: The patient's blood contains amplifiable C. glabrata DNA. In addition, a faint band appears on an agarose gel from this patient's amplified sample, in the lane containing the species-specific primers for amplification of C. glabrata.
All positive and negative controls worked as predicted.

---

What is claimed is:

1. An isolated DNA segment having a DNA sequence selected from the group consisting of:

5'-GAC AGC TAC GCA AAT CAA ACA G-3'

5'-GTC AAT TGC TGA CGA AAG TCA GCG-3'

5'-CAG ACA GAC AGA CAG ACA GAC ACA C-3'

5'-GAT CTG GAT ACT CTG TTC CAA GTC-3'

5'-GCG CGA GAA CGG GGA CAG AAA AAA TAC AC-3'

5'-GTG CAG ATA TGT CGC TAT TAC CTT TGG-3'

5'-GAC GGA CGA CCT GCT TCC GAT TCT CAT AGA-3'

5'-GGT TGA CAC TTC GCA TAC-3'

5'-CGT ATG TGA CCA GTG AC-3'

5'-GTA GGT TCG ACA AGG ATG A-3'

(See SEQ ID NOS:7–16, respectively)
   and complementary sequences thereof.

2. An isolated DNA segment of claim 1 which is labelled.

3. An isolated DNA segment of claim 2 wherein the label is fluorescent.

4. An isolated DNA segment of claim 2 wherein the label is digoxigenin-dUTP.

5. An isolated DNA segment of claim 2 wherein the label is biotin.

6. An isolated DNA segment of claim 2 which is radio-labeled.

7. A PCR-based amplification kit for candida comprising at least one primer pair selected from:

*Candida parapsilosis* (See SEQ ID NOS:5 and 7, respectively)

CP-5' primer: 5'-GAG GCT GTG ATG TGT GCT GTT GAC CAG-3'

CP-3' primer: 5'-GAC AGC TAC GCA AAT CAA ACA G-3';

*Candida tropicalis* (See SEQ ID NOS:9 and 10, respectively)

CT-5' primer: 5'-CAG ACA GAC AGA CAG ACA GAC ACA C-3'

CT-3' primer: 5'-GAT CTG GAT ACT CTG TTC CAA GTC-3';

*Candida glabrata* (See SEQ ID NOS:4 and 12, respectively)

CG-5' primer: 5'-CGA CTG GTT GAC GAT AAT CAG AGG AGA TGG G-3'

CG-3' primer: 5'-GTG CAG ATA TGT CGC TAT TAC CTT TGG-3';

*Candida krusei* (See SEQ ID NOS:14 and 15, respectively)

CK-5' primer: 5'-GGT TGA CAC TTC GCA TAC-3'

CK-3' primer: 5'-CGT ATG TGA CCA GTG AC-3';

and complementary sequences thereof; together with buffer and polymerase.

8. A PCR-based diagnostic kit for candida comprising at least one primer pair and corresponding species-specific probe selected from:

*Candida parapsilosis* (See SEQ ID NOS:5, 7 and 8, respectively)

CP-5' primer: 5'-GAG GCT GTG ATG TGT GCT GTT GAC CAG-3'

CP-3' primer: 5'-GAC AGC TAC GCA AAT CAA ACA G-3'CP probe: 5'-GTC AAT TGC TGA CGA AAG TCA GCG-3';

*Candida tropicalis* (See SEQ ID NOS:9, 10 and 11, respectively)

CT-5' primer: 5'-CAG ACA GAC AGA CAG ACA GAC ACA C-3'

CT-3' primer: 5'-GAT CTG GAT ACT CTG TTC CAA GTC-3'

CT probe: 5'-GCG CGA GAA CGG GGA CAG AAA AAA TAC AC-3';

*Candida glabrata* (See SEQ ID NOS:4, 12 and 13, respectively)

CG-5' primer: 5'-CGA CTG GTT GAC GAT AAT CAG AGG AGA TGG G-3'

CG-3' primer: 5'-GTG CAG ATA TGT CGC TAT TAC CTT TGG-3'

CG probe: 5'-GAC GGA CGA CCT GCT TCC GAT TCT CAT AGA-3';

*Candida krusei* (See SEQ ID NOS:14, 15 and 16, respectively)

CK-5' primer: 5'-GGT TGA CAC TTC GCA TAC-3'

CK-3' primer: 5'-CGT ATG TGA CCA GTG AC-3'

CK probe: 5'-GTA GGT TCG ACA AGG ATG A-3';

and complementary sequences thereof;
together with buffer and polymerase, wherein the DNA sequence of said species-specific probe hybridizes to a portion of the DNA of *Candida parapsilosis, Candida tropicalis, Candida glabrata, Candida krusei* respectively.

9. A diagnostic kit for candida comprising at least one species-specific probe selected from:

*Candida parapsilosis* (See SEQ ID NO:8)

CP probe: 5'-GTC AAT TGC TGA CGA AAG TCA GCG-3';

*Candida tropicalis* (see SEQ ID NO:1)

CT probe: 5'-GCG CGA GAA CGG GGA CAG AAA AAA TAC AC-3';

*Candida glabrata* (See SEQ ID NO:13)

CG probe: 5'-GAC GGA CGA CCT GCT TCC GAT TCT CAT AGA-3';

*Candida krusei* (See SEQ ID NO:16)

CK probe: 5'-GTA GGT TCG ACA AGG ATG A-3;

and complementary sequences thereof;
wherein the DNA sequence of said species-specific probe hybridizes to a portion of the DNA of *Candida parapsilosis, Candida tropicalis, Candida glabrata, Candida krusei* respectively.

10. The kit of claim 8 or 9 wherein said probe is labeled.

11. The kit of claim 10 wherein the probe label is fluorescent.

12. The kit of claim 10 wherein the probe label is digoxigenin-dUTP.

13. The kit of claim 10 wherein the probe label is biotin.

14. The kit of claim 10 wherein said probe is radiolabeled.

15. The kit of claim 8 or 9 wherein said probe is immobilized to a surface.

16. The kit of claim 15 wherein the surface is a separable bead.

17. The kit of claim 15 wherein the surface is the well of a diagnostic plate.

18. The kit of claim 7 or 8 wherein the kit further comprises an internal standard for accessing relative amounts of candida after amplification.

19. A method for quantifying one or more species of candida contained in a sample comprising the steps of:

i) collecting a sample suspected of containing a candida species;

ii) preparing said sample for PCR amplification;

iii) adding PCR reagents to said prepared sample, including at least one primer pair selected from:

*Candida parapsilosis* (See SEQ ID NOS:5 and 7, respectively)

CP-5' primer: 5'-GAG GCT GTG ATG TGT GCT GTT GAC CAG-3'

CP-3' primer: 5'-GAC AGC TAC GCA AAT CAA ACA G-3';

*Candida tropicalis* (See SEQ ID NOS:9 and 10, respectively)

CT-5' primer: 5'-CAG ACA GAC AGA CAG ACA GAC ACA C-3'

CT-3' primer: 5'-GAT CTG GAT ACT CTG TTC CAA GTC-3';

*Candida glabrata* (see SEQ ID NOS:4 and 12, respectively)

CG-5' primer: 5'-CGA CTG GTT GAC GAT AAT CAG AGG AGA TGG G-3'

CG-3' primer: 5'-GTG CAG ATA TGT CGC TAT TAC CTT TGG-3';

*Candida krusei* (See SEQ ID NOS:14 and 15, respectively)

CK-5' primer: 5'-GGT TGA CAC TTC GCA TAC-3'

CK-3' primer: 5'-CGT ATG TGA CCA GTG AC-3';

and complementary sequences thereof;
iv) maintaining the prepared sample of step iii) under conditions suitable for amplification;
v) adding at least one labeled candida species-specific probe, corresponding to said at least one primer pair, selected from:
*Candida parapsilosis* (see SEQ ID NO:8)

CP probe: 5'-GTC AAT TGC TGA CGA AAG TCA GCG-3';

*Candida tropicalis* (See SEQ ID NO:1)

CT probe: 5'-GCG CGA GAA CGG GGA CAG AAA AAA TAC AC-3';

*Candida glabrata* (See SEQ ID NO:13)

CG probe: 5'-GAC GGA CGA CCT GCT TCC GAT TCT CAT AGA-3';

*Candida krusei* (See SEQ ID NO:16)

CK probe: 5'-GTA GGT TCG ACA AGG ATG A-3';

and complementary sequences thereof;
vi) measuring quantitatively one or more of the candida species contained in the sample.

20. The method of claim 19 additionally comprising adding to step iii) an internal standard for accessing relative amounts of candida after amplification.

21. The method of claim 19 wherein at least one species-specific probe of step (v) is labelled with a fluorescent label.

22. The method of claim 19 wherein at least one species-specific probe of step (v) is labelled with digoxigenin-dUTP.

23. The method of claim 19 wherein at least one species-specific probe of step (v) are labelled with biotin.

24. The method of claim 19 wherein at least one species-specific probe of step (v) is radiolabeled.

25. A method for detecting one or more species of candida contained in a sample comprising the steps of:
i) collecting a sample suspected of containing a candida species;
ii) preparing said sample for PCR amplification;
iii) adding PCR reagents to said prepared sample, including at least one primer pair selected from:
*Candida parapsilosis* (See SEQ ID NOS:5 and 7, respectively)

CP-5' primer: 5'-GAG GCT GTG ATG TGT GCT GTT GAC CAG-3'

CP-3' primer: 5'-GAC AGC TAC GCA AAT CAA ACA G-3';

*Candida tropicalis* (See SEQ ID NOS:9 and 10, respectively)

CT-5' primer: 5'-CAG ACA GAC AGA CAG ACA GAC ACA C-3'

CT-3' primer: 5'-GAT CTG GAT ACT CTG TTC CAA GTC-3';

*Candida glabrata* (see SEQ ID NOS:4 and 12, respectively)

CG-5' primer: 5'-CGA CTG GTT GAC GAT AAT CAG AGG AGA TGG G-3'

CG-3' primer: 5'-GTG CAG ATA TGT CGC TAT TAC CTT TGG-3';

*Candida krusei* (See SEQ ID NOS:14 and 15, respectively)

CK-5' primer: 5'-GGT TGA CAC TTC GCA TAC-3'

CK-3' primer: 5'-CGT ATG TGA CCA GTG AC-3';

and complementary sequences thereof;
iv) maintaining the prepared sample of step iii) under conditions suitable for amplification;
v) adding at least one labeled candida species-specific probe, corresponding to said at least one primer pair, selected from:
*Candida parapsilosis* (See SEQ ID NO:8)

CP probe: 5'-GTC AAT TGC TGA CGA AAG TCA GCG-3';

*Candida tropicalis* (See SEQ ID NO:1)

CT probe: 5'-GCG CGA GAA CGG GGA CAG AAA AAA TAC AC-3';

*Candida glabrata* (see SEQ ID NO:13)

CG probe: 5'-GAC GGA CGA CCT GCT TCC GAT TCT CAT AGA-3';

*Candida krusei* (See SEQ ID NO:16)

CK probe: 5'-GTA GGT TCG ACA AGG ATG A-3';

and complementary sequences thereof;
vi) detecting one or more of the candida species contained in the sample.

26. The method of claim 25 wherein at least one species-specific probe of step (v) is labelled with a fluorescent label.

27. The method of claim 25 wherein at least one species-specific probe of step (v) is labelled with digoxigenin-dUTP.

28. The method of claim 25 wherein at least one species-specific probe of step (v) is labelled with biotin.

29. The method of claim 25 wherein at least one species-specific probe of step (v) is radiolabeled.

30. A method of selecting an appropriate dosage or type of antifungal agent for treating an infection caused by candida comprising the steps of:
i) obtaining a sample from a patient to be treated;
ii) preparing said sample for PCR amplification;
iii) adding PCR reagents to said prepared sample, including at least one primer pair selected from:
*Candida parapsilosis* (See SEQ ID NOS:5 and 7, respectively)

CP-5' primer: 5'-GAG GCT GTG ATG TGT GCT GTT GAC CAG-3'

CP-3' primer: 5'-GAC AGC TAC GCA AAT CAA ACA G-3';

*Candida tropicalis* (See SEQ ID NOS:9 and 10, respectively)

CT-5' primer: 5'-CAG ACA GAC AGA CAG ACA GAC ACA C-3'

CT-3' primer: 5'-GAT CTG GAT ACT CTG TTC CAA GTC-3';

*Candida glabrata* (see SEQ ID NOS:4 and 12, respectively)

CG-5' primer: 5'-CGA CTG GTT GAC GAT AAT CAG AGG AGA TGG G-3'

CG-3' primer: 5'-GTG CAG ATA TGT CGC TAT TAC CTT TGG-3';

*Candida krusei* (See SEQ ID NOS:14 and 15, respectively)

CK-5' primer: 5'-GGT TGA CAC TTC GCA TAC-3'

CK-3' primer: 5'-CGT ATG TGA CCA GTG AC-3';

and complementary sequences thereof;

iv) maintaining the prepared sample of step iii) under conditions suitable for amplification;

v) adding at least one labeled candida species-specific probe corresponding to said primer pair, selected from:
*Candida parapsilosis* (See SEQ ID NO:8)

CP probe: 5'-GTC AAT TGC TGA CGA AAG TCA GCG-3';

*Candida tropicalis* (See SEQ ID NO:1)

CT probe: 5'-GCG CGA GAA CGG GGA CAG AAA AAA TAC AC-3';

*Candida glabrata* (See SEQ ID NO:13)

CG probe: 5'-GAC GGA CGA CCT GCT TCC GAT TCT CAT AGA-3';

*Candida krusei* (See SEQ ID NO:16)

CK probe: 5'-GTA GGT TCG ACA AGG ATG A-3';

and complementary sequences thereof;

vi) measuring quantitatively one or more of the candida species contained in the sample;

vii) selecting the type or adjusting the dosage of said antifungal agent based on the quantitative measurement.

31. The method of claim 30 additionally comprising adding to step iii) an internal standard for accessing relative amounts of candida after amplification.

32. The method of claim 30 wherein at least one species-specific probe of step (v) is labelled with a fluorescent label.

33. The method of claim 30 wherein at least one species-specific probe of step (v) is labelled with digoxigenin-dUTP.

34. The method of claim 30 wherein at least one species-specific probe of step (v) is labelled with biotin.

35. The method of claim 30 wherein at least one species-specific probe of step (v) is radiolabeled.

36. In a process for preparing a plate for detecting and identifying candida species, the improvement comprising synthesizing a primer with a biotin label on its 5' end, said primer having a sequence selected from the following sequences:

5'-CGC CTC TTG ATG GTG ATG AT-3';

5'-TCC GGT ATC ACC TGG CTC-3';

5'-GAG GCT GTG ATG TGT GCT GTT GAC CAG-3';

5'-GAC AGC TAC GCA AAT CAA ACA G-3';

5'-CAG ACA GAC AGA CAG ACA GAC ACA C-3';

5'-GAT CTG GAT ACT CTG TTC CAA GTC-3';

5'-CGA CTG GTT GAC GAT AAT CAG AGG AGA TGG G-3';

5'-GTG CAG ATA TGT CGC TAT TAC CTT TGG-3';

5'-GGT TGA CAC TTC GCA TAC-3';

5'-CGT ATG TGA CCA GTG AC-3';

(See SEQ ID NO:16)

and complementary sequences thereof; incorporating the synthesized biotinylated primer into one strand of the double-stranded DNA product, bonding the double-stranded DNA product with the incorporated biotin label into the wells of a Streptavidin coated microtiter plate, treating the double-stranded product with a dilute NaOH solution to dissociate the two strands, and removing the unlabeled and unbound strand of DNA, thereby leaving the single-stranded, biotin-labeled product bound to the plate.

37. The plate for detecting and identifying candida species prepared according to claim 36.

38. In a process for detecting and identifying candida species, the improvement comprising contacting a sample suspected of containing candida with the plate of claim 37, hybridizing the contacted plate with a species-specific oligonucleotide probe that is 3' tailed labeled with digoxigenin dUTP, and detecting and visualizing the presence of the captured, hybridized product with an alkaline phosphatase conjugated antidigoxigenin antibody.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CGCCTCTTGA TGGTGATGAT      20

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TCCGGTATCA CCTGGCTC      18

```
(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGTTCGTACT AGAGTTGTGT TGTTTTGGAT                                  30

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGACTGGTTG ACGATAATCA GAGGAGATGG G                                31

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAGGCTGTGA TGTGTGCTGT TGACCAG                                     27

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGGCTTGCTC TTTGTCGGGC GAGCGAACG                                   29

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GACAGCTACG CAAATCAAAC AG                                          22

(2) INFORMATION FOR SEQ ID NO:8:

(i) SEQUENCE CHARACTERISTICS:
        (A) LENGTH: 24 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTCAATTGCT GACGAAAGTC AGCG                                              24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CAGACAGACA GACAGACAGA CACA                                              24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GATCTGGATA CTCTGTTCCA AGTC                                              24

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCGCGAGAAC GGGGACAGAA AAAATACAC                                         29

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTGCAGATAT GTCGCTATTA CCTTTGG                                           27

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)
```

```
      (xi) SEQUENCE DESCRIPTION: SEQ ID NO:13:

GACGGACGAC CTGCTTCCGA TTCTCATAGA                                           30

(2) INFORMATION FOR SEQ ID NO:14:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:14:

GGTTGACACT TCGCATAC                                                        18

(2) INFORMATION FOR SEQ ID NO:15:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:15:

CGTATGTGAC CAGTGAC                                                         17

(2) INFORMATION FOR SEQ ID NO:16:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:16:

GTAGGTTCGA CAAGGATGA                                                       19
```